(12) United States Patent
Okano et al.

(10) Patent No.: US 11,855,418 B2
(45) Date of Patent: Dec. 26, 2023

(54) DISCHARGE DEVICE WITH MINIMAL NOISE GENERATION

(71) Applicant: SHARP KABUSHIKI KAISHA, Sakai (JP)

(72) Inventors: Satoshi Okano, Sakai (JP); Nobuyuki Ohe, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 17/971,631

(22) Filed: Oct. 23, 2022

(65) Prior Publication Data

US 2023/0198233 A1 Jun. 22, 2023

(30) Foreign Application Priority Data

Nov. 17, 2021 (JP) ................. 2021-187087

(51) Int. Cl.
*H01T 23/00* (2006.01)
*H01T 19/04* (2006.01)
*A61L 9/22* (2006.01)
*H01J 27/26* (2006.01)
*H01J 27/22* (2006.01)

(52) U.S. Cl.
CPC ............... *H01T 23/00* (2013.01); *A61L 9/22* (2013.01); *H01J 27/22* (2013.01); *H01J 27/26* (2013.01); *H01T 19/04* (2013.01)

(58) Field of Classification Search
CPC .. H01T 23/00; H01T 19/00; A61L 9/22; H01J 33/00; B03C 3/68
See application file for complete search history.

(56) References Cited

U.S. PATENT DOCUMENTS

| | | | |
|---|---|---|---|
| 2007/0091536 A1* | 4/2007 | Kato | H01T 23/00 361/231 |
| 2016/0104595 A1* | 4/2016 | Nishida | H01J 27/022 313/230 |
| 2018/0053620 A1* | 2/2018 | Nishida | H01J 27/26 |
| 2020/0054780 A1* | 2/2020 | Ezaki | A61L 9/22 |
| 2021/0128775 A1* | 5/2021 | Ohe | H01T 23/00 |
| 2023/0149591 A1* | 5/2023 | Okano | A61L 9/22 361/229 |

FOREIGN PATENT DOCUMENTS

WO 2018055783 A1 3/2018

* cited by examiner

*Primary Examiner* — Tracie Y Green
(74) *Attorney, Agent, or Firm* — ScienBiziP, P.C.

(57) ABSTRACT

A discharge device includes a connector portion, an electrode portion, and a housing portion. A voltage is applied to the connector portion externally. The electrode portion discharges by boosting and supplying a voltage from the connector portion. The housing portion houses the connector portion and the electrode portion. The housing portion includes a step portion between the connector portion and the electrode portion. The step portion is, for example, a recess.

6 Claims, 11 Drawing Sheets

DISCHARGE DEVICE WITH MINIMAL NOISE GENERATION

CROSS-REFERENCE TO RELATED APPLICATIONS

This application claims the benefit of priority to Japanese Patent Application Number 2021-187087 filed on Nov. 17, 2021. The entire contents of the above-identified application are hereby incorporated by reference.

BACKGROUND

Technical Field

The disclosure relates to a discharge device.

A discharge device described in WO 2018/055783 includes a connector, a discharge electrode, and a housing. A voltage is applied externally through the connector. The discharge electrode discharges by boosting and supplying the voltage from the connector.

SUMMARY

In the discharge device described in WO 2018/055783, a path serving as a reference for a creepage distance between the connector and the discharge electrode is flat. More specifically, between the connector and the discharge electrode, surfaces along side walls of the housing are flat.

While the discharge device described in WO 2018/055783 operates without any issues because the discharge electrode (electrode portion) is distanced from the connector (connector portion), a high voltage produced by discharge is likely to propagate to the connector when the distance between the discharge electrode (electrode portion) and the connector (connector portion) is short. This high voltage may cause noise to be generated, which may adversely affect peripheral components.

The disclosure has been made in view of the above problem, and an object thereof is to provide a discharge device that can prevent noise caused by a high voltage from being generated and adversely affecting peripheral components.

According to an aspect of the disclosure, a discharge device includes a connector portion, an electrode portion, and a housing portion. A voltage is applied externally through the connector portion. The electrode portion discharges by boosting the voltage from the connector portion to a voltage value with a desired waveform and supplying the boosted voltage. The housing portion houses the connector portion and the electrode portion. The housing portion includes a step portion between the connector portion and the electrode portion.

According to the discharge device of the disclosure, it is possible to prevent noise caused by a high voltage from being generated and adversely affecting the peripheral components.

BRIEF DESCRIPTION OF DRAWINGS

The disclosure will be described with reference to the accompanying drawings, wherein like numbers reference like elements.

DESCRIPTION OF EMBODIMENTS

Figure 1:
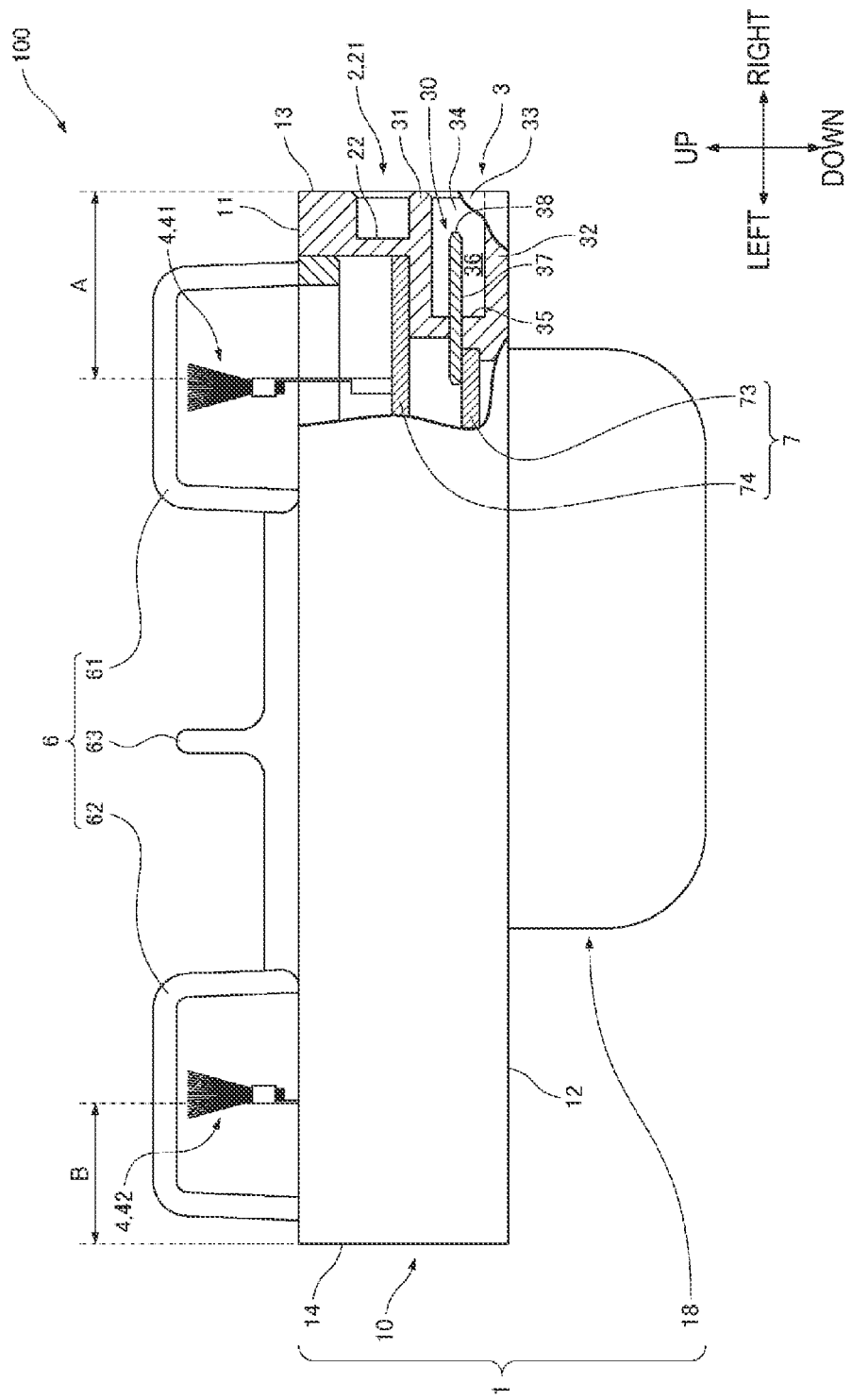
FIG. 1 is a partially cut-out front view illustrating a discharge device according to a first embodiment.

Embodiments of the disclosure will be described hereinafter with reference to the accompanying drawings. Note that, in the drawings, the same or equivalent components are denoted by the same reference signs and description thereof will not be repeated. In the following description, even in a case where a term indicating a specific position or direction such as "up", "down", "left", "right", "front", or "rear" is used, these terms are used for convenience to facilitate understanding of the contents of the embodiments, and are not related to the directions at the time of actual implementation.

First Embodiment

A discharge device 100 according to a first embodiment of the disclosure will be described with reference to FIG. 1 to FIG. 3.

FIG. 1 is a partially cut-out front view illustrating the discharge device 100 of the first embodiment. FIG. 2 is a right side view illustrating the discharge device 100 of the first embodiment. FIG. 3 is a perspective view illustrating the discharge device 100 of the first embodiment.

As illustrated in FIG. 1, the discharge device 100 includes a connector portion 3, an electrode portion 4, and a housing portion 1. A voltage is applied to the connector portion 3 externally. The electrode portion 4 discharges by boosting the voltage from the connector portion 3 to a voltage value with a desired waveform and supplying the boosted voltage. The housing portion 1 houses the connector portion 3 and the electrode portion 4. The housing portion 1 includes a step portion 2 between the connector portion 3 and the electrode portion 4.

By providing the step portion 2 between the connector portion 3 and the electrode portion 4, the creepage distance between the connector portion 3 and the electrode portion 4 is long. Herein, the creepage distance between the connector portion 3 and the electrode portion 4 is the shortest distance between the connector portion 3 and the electrode portion 4 at a surface along the housing portion 1. Thus, when the creepage distance is long, a high voltage produced by discharge is less likely to propagate from the electrode portion 4 to the connector portion 3. As a result, it is possible to prevent noise from being generated by a high voltage and adversely affecting peripheral components.

The discharge device 100 further includes an electrode protecting section 6 and an electronic component group 7.

The electrode protecting section 6 protects the electrode portion 4. The electronic component group 7 electrically connects the connector portion 3 and the electrode portion 4. To enable discharge at the electrode portion 4, the electronic component group 7 includes various electronic components (not illustrated), which are mounted on a substrate, and supplies a boosted voltage to the electrode portion 4.

The housing portion 1 is a housing having insulating properties. The housing portion 1 is formed of, for example, resin. The housing portion 1 includes a main housing portion 10 and a sub housing portion 18. The main housing portion 10 has a substantially rectangular parallelepiped shape with a longitudinal direction extending in the left-right direction. The main housing portion 10 has an upper surface 11, a lower surface 12, a right side surface 13, and a left side surface 14. Hereinafter, the right side surface 13 and the left side surface 14 are referred to as a first side surface 13 and a second side surface 14, respectively.

The connector portion 3 is disposed at the first side surface 13. The step portion 2 is disposed above the connector portion 3 at the first side surface 13. The electrode portion 4 and the electrode protecting section 6 are disposed on the upper surface 11. The sub housing portion 18 projects from the lower surface 12. When the connector portion 3 and the step portion 2 are disposed at the first side surface 13 and the electrode portion 4 is disposed on the upper surface 11, a long creepage distance can be ensured despite the connector portion 3 being close to the electrode portion 4. This makes it possible to simplify the electronic component group 7 that electrically connects the connector portion 3 and the electrode portion 4.

The connector portion 3 includes a port 30 and a terminal portion 37. The port 30 has insulating properties. The port 30 is formed of, for example, resin. The port 30 is formed integrally with the main housing portion 10, for example. The port 30 includes an upper wall 31, a lower wall 32, a front wall 33, and a rear wall 34. The port 30 further includes an inner wall 35. The inner wall 35 connects the upper wall 31, the lower wall 32, the front wall 33, and the rear wall 34 at an inner side (left side). The right end surfaces of the upper wall 31, the lower wall 32, the front wall 33, and the rear wall 34 are flush with the first side surface 13. The port 30 includes a port space 36. The port space 36 is surrounded by the upper wall 31, the lower wall 32, the front wall 33, the rear wall 34, and the inner wall 35. The port space 36 is a space into which an external connector (for example, a housing) for applying a voltage is plugged (not illustrated).

The terminal portion 37 is electrically connected to the electrode portion 4 by the electronic component group 7. The terminal portion 37 extends through the inner wall 35. A right end 38 of the terminal portion 37 is located further inward (further to the left) than the first side surface 13. Accordingly, the right portion of the terminal portion 37 is located in the port space 36. The left portion of the terminal portion 37 is connected to the electronic component group 7. The terminal portion 37 is, for example, a plurality of metal pins.

The electronic component group 7 includes, for example, a control substrate 73, a high-voltage substrate 74, and other electronic component groups (not illustrated). The control substrate 73 and the high-voltage substrate 74 are housed in the main housing portion 10. The other electronic component groups are housed in the main housing portion 10 or the sub housing portion 18. The control substrate 73 is connected to the left portion of the terminal portion 37 at the left of the inner wall 35. Thus, a voltage is applied to the control substrate 73 from the terminal portion 37. The other electronic component groups are mounted on the control substrate 73, and boost the voltage. The high-voltage substrate 74 supplies the boosted voltage (that is, a high voltage) to the electrode portion 4.

Figure 2:
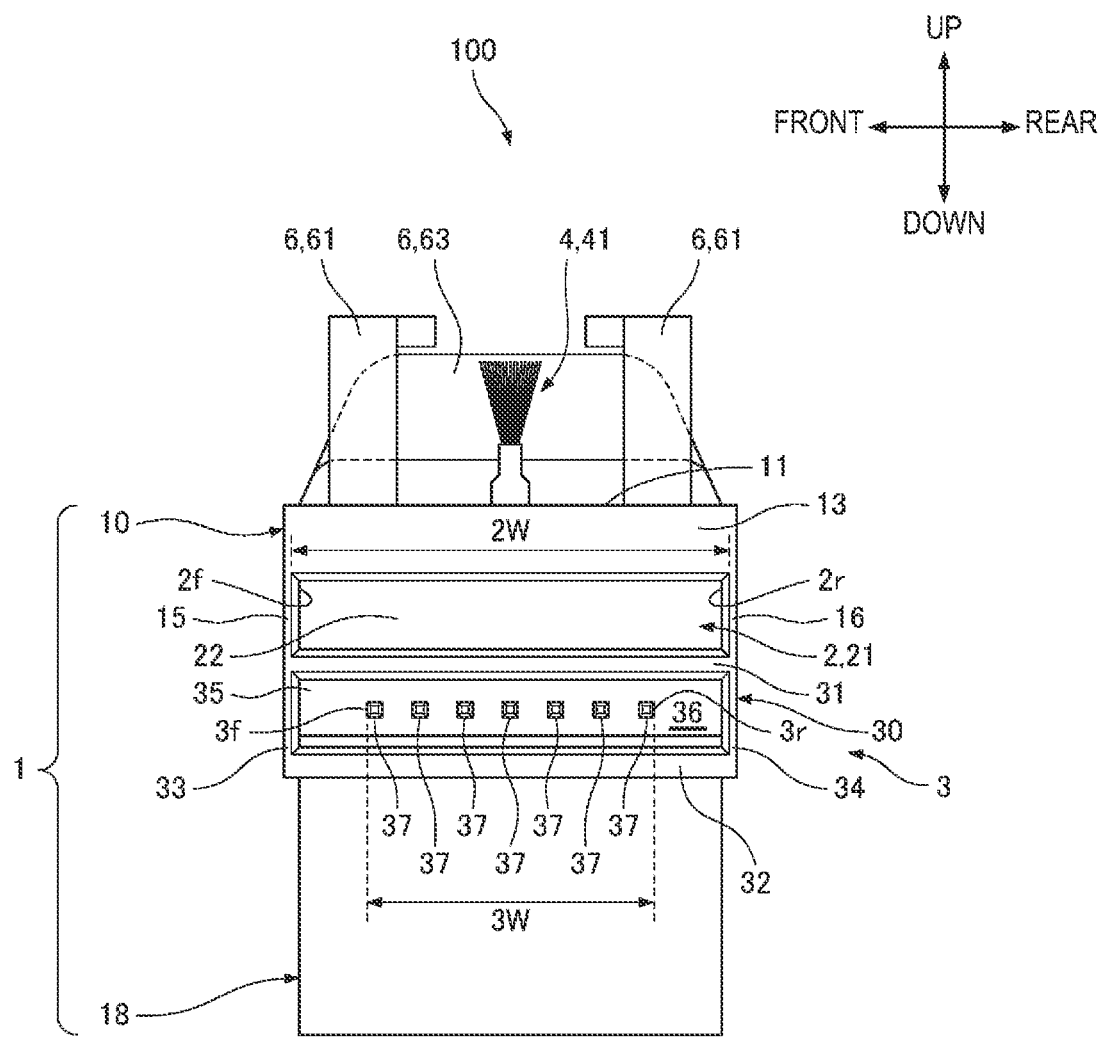
FIG. 2 is a right side view illustrating the discharge device according to the first embodiment.

As illustrated in FIG. 2, the step portion 2 is a recess 21 formed in the first side surface 13. Since the step portion 2 is the recess 21, the overall contour of the housing portion 1 does not largely change. Thus, the versatility of the discharge device 100 can be maintained. A bottom 22 of the recess 21 is preferably located further left (inward) than the right end 38 of the terminal portion 37 to increase the creepage distance. As illustrated in FIGS. 2 and 3, the recess 21 does not reach a front end and a rear end of the main housing portion 10. In other words, the recess 21 is sandwiched in the front-rear direction between a front end piece 15 and a rear end piece 16 of the main housing portion 10.

The recess 21 has a rectangular shape with the front-rear direction as a longitudinal direction. The recess 21 is wider than the terminal portion 37 in the front-rear direction. That is, a width 2W of the recess 21 in the front-rear direction is larger than a width 3W of the terminal portion 37 in the front-rear direction (2W>3W). Note that the front-rear direction corresponds to a direction orthogonal to a direction along a creepage distance between the electrode portion 4 and the terminal portion 37. Since the recess 21 is wider than the terminal portion 37 in the front-rear direction, the path of a high voltage that may propagate from the electrode portion 4 to the terminal portion 37 passes through the recess 21. Thus, it is further possible to prevent noise from being generated by the high voltage and adversely affecting peripheral components. The recess 21 being wider than the terminal portion 37 is not limited to width in the front-rear direction; it is sufficient that the recess 21 be wider in a direction intersecting a direction along the creepage distance.

It is preferable that a front end $2f$ of the recess 21 be located further frontward than a front end $3f$ of the terminal portion 37, and a rear end $2r$ of the recess 21 be located further rearward than a rear end $3r$ of the terminal portion 37. With such a configuration, the path of the high voltage that may propagate from the electrode portion 4 to the terminal portion 37 reliably passes through the recess 21. Therefore, it is further possible to prevent noise from being generated by the high voltage and adversely affecting peripheral components.

Figure 3:
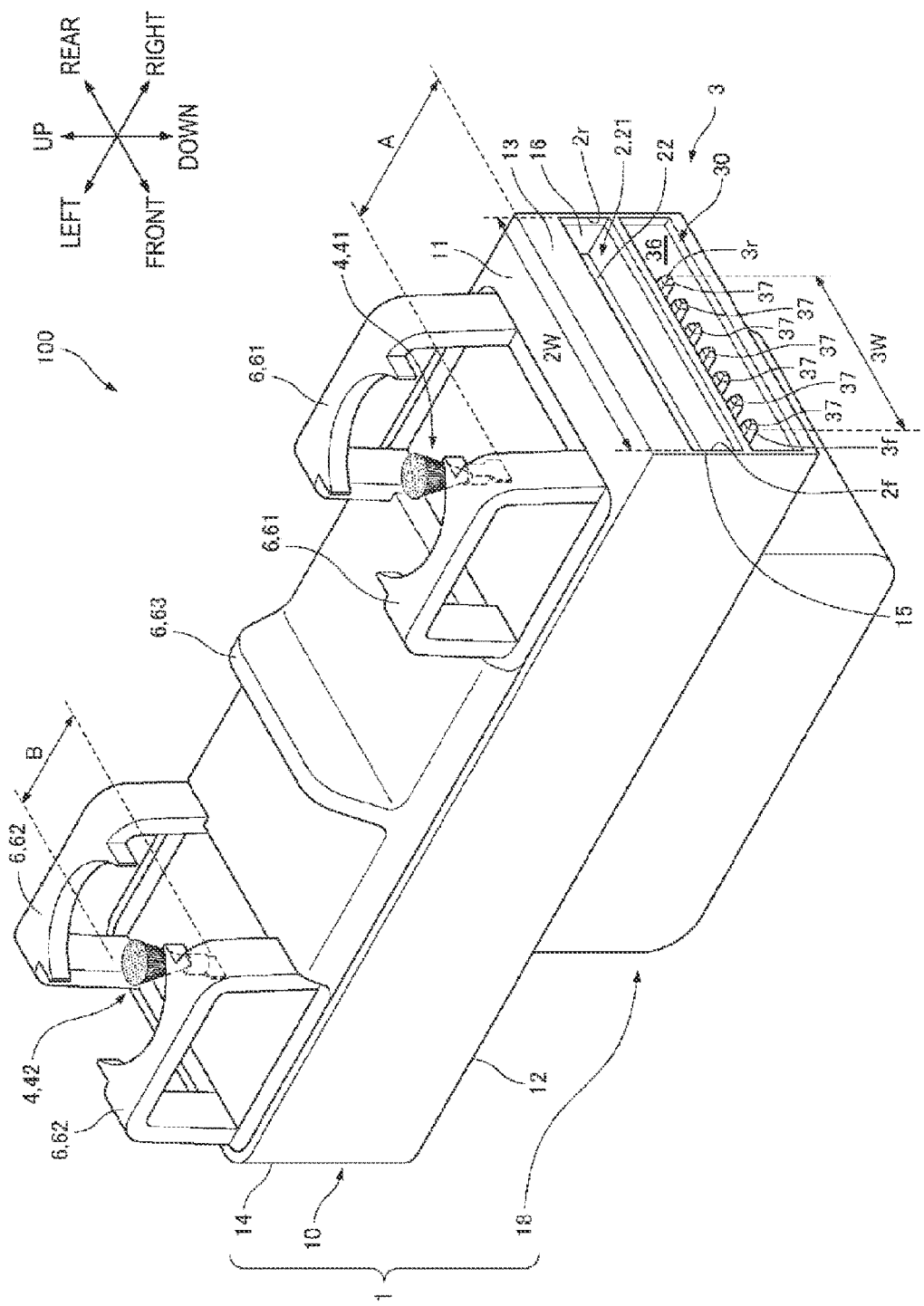
FIG. 3 is a perspective view illustrating the discharge device according to the first embodiment.

As illustrated in FIG. 3, the electrode portion 4 includes a first electrode 41 and a second electrode 42. The first electrode 41 and the second electrode 42 are brush-shaped electrodes. The first electrode 41 and the second electrode 42 may be needle-shaped electrodes. One of the first electrode 41 and the second electrode 42 may be a dielectric electrode surrounding a needle electrode. When a high voltage is applied to the first electrode 41 and the second electrode 42, corona is generated. That is, each of the first electrode 41 and the second electrode 42 discharges to generate ions. Accordingly, the first electrode 41 and the second electrode 42 are also referred to as discharge electrodes.

For example, one of the first electrode 41 and the second electrode 42 releases positive ions by discharging. Here, the positive ion is a cluster ion [$H^+(H_2O)_m$, where m is any integer equal to or greater than zero] in which a plurality of water molecules are clustered around a hydrogen ion ($H^+$). Further, for example, the other one of the first electrode 41 and the second electrode 42 releases negative ions by discharging. Here, the negative ion is a cluster ion [$O_2^-$ (H$_2$O)$_n$, where n is any integer equal to or greater than zero] in which the plurality of water molecules are clustered around an oxygen ion (O$_2^-$).

When the first electrode 41 and the second electrode 42 release positive ions and negative ions respectively, as an interval between the first electrode 41 and the second electrode 42 is larger, it is possible to suppress the neutralization of the ions released from the first electrode 41 and the second electrode 42 and a higher ion amount can be maintained.

The released positive ions and negative ions individually surround, for example, mold bacteria floating in the air and cause chemical reactions on the surfaces of the mold bacteria. Active species hydroxyl radicals (—OH) are produced by the chemical reactions. The mold bacteria are removed by the action of these hydroxyl radicals (—OH).

The first electrode 41 is disposed on the right portion of the upper surface 11 of the main housing portion 10 (closer to the first side surface 13). The second electrode 42 is disposed on the left portion of the upper surface 11 of the main housing portion 10 (closer to the second side surface 14). That is, the first electrode 41 is closer to the first side surface 13 than to the second side surface 14. The second electrode 42 is closer to the second side surface 14 than to the first side surface 13. A distance A between the first electrode 41 and the first side surface 13 is longer than a distance B between the second electrode 42 and the second side surface 14 (A>B). This increases the creepage distance on the upper surface 11 of the housing portion 1. Thus, due to the longer creepage distance, the high voltage produced by discharge is even less likely to propagate from the electrode portion 4 to the connector portion 3. As a result, it is possible to further prevent noise from being generated by the high voltage and adversely affecting peripheral components.

The electrode protecting section 6 includes a first protecting body 61, a second protecting body 62, and a wall member 63. The first protecting body 61 is erected on the right portion of the upper surface 11 of the main housing portion 10. The first protecting body 61 protects the first electrode 41. The second protecting body 62 is erected on the left portion of the upper surface 11 of the main housing portion 10. The second protecting body 62 protects the second electrode 42. The wall member 63 is disposed between the first electrode 41 and the second electrode 42. The wall member 63 lengthens the leakage path of a current that may be produced between the first electrode 41 and the second electrode 42. The wall member 63 also functions as a wall for suppressing the neutralization of the positive and negative ions released into the space.

Second Embodiment

Next, a discharge device 100 according to a second embodiment of the disclosure will be described with reference to FIG. 4. In the second embodiment, the shape of the step portion 2 is different from that in the first embodiment. Differences between the second embodiment and the first embodiment will be described below.

Figure 4:
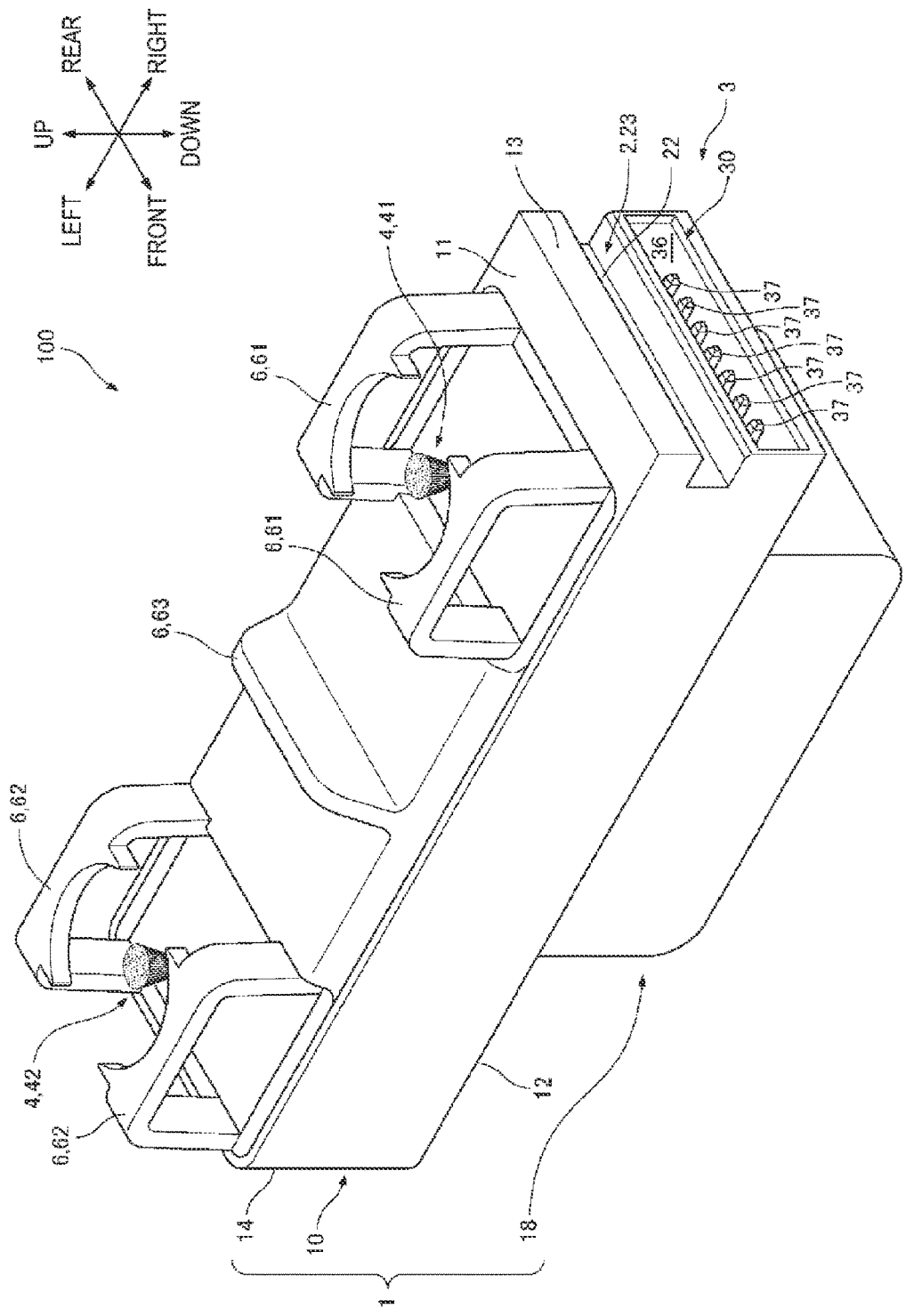
FIG. 4 is a perspective view illustrating a discharge device according to a second embodiment.

FIG. 4 is a perspective view illustrating the discharge device 100 of the second embodiment. As illustrated in FIG. 4, the step portion 2 is a recess 23 extending to the front end and the rear end of the main housing portion 10. With this configuration, the path of a high voltage that may propagate from the electrode portion 4 to the terminal portion 37 reliably passes through the recess 23. Therefore, it is possible to further prevent noise from being generated by the high voltage and adversely affecting peripheral components.

Third Embodiment

Next, a discharge device 100 according to a third embodiment of the disclosure will be described with reference to FIG. 5. In the third embodiment, the shape of the step portion 2 is different from that in the first and second embodiments. Differences between the third embodiment and the first and second embodiments will be described below.

Figure 5:
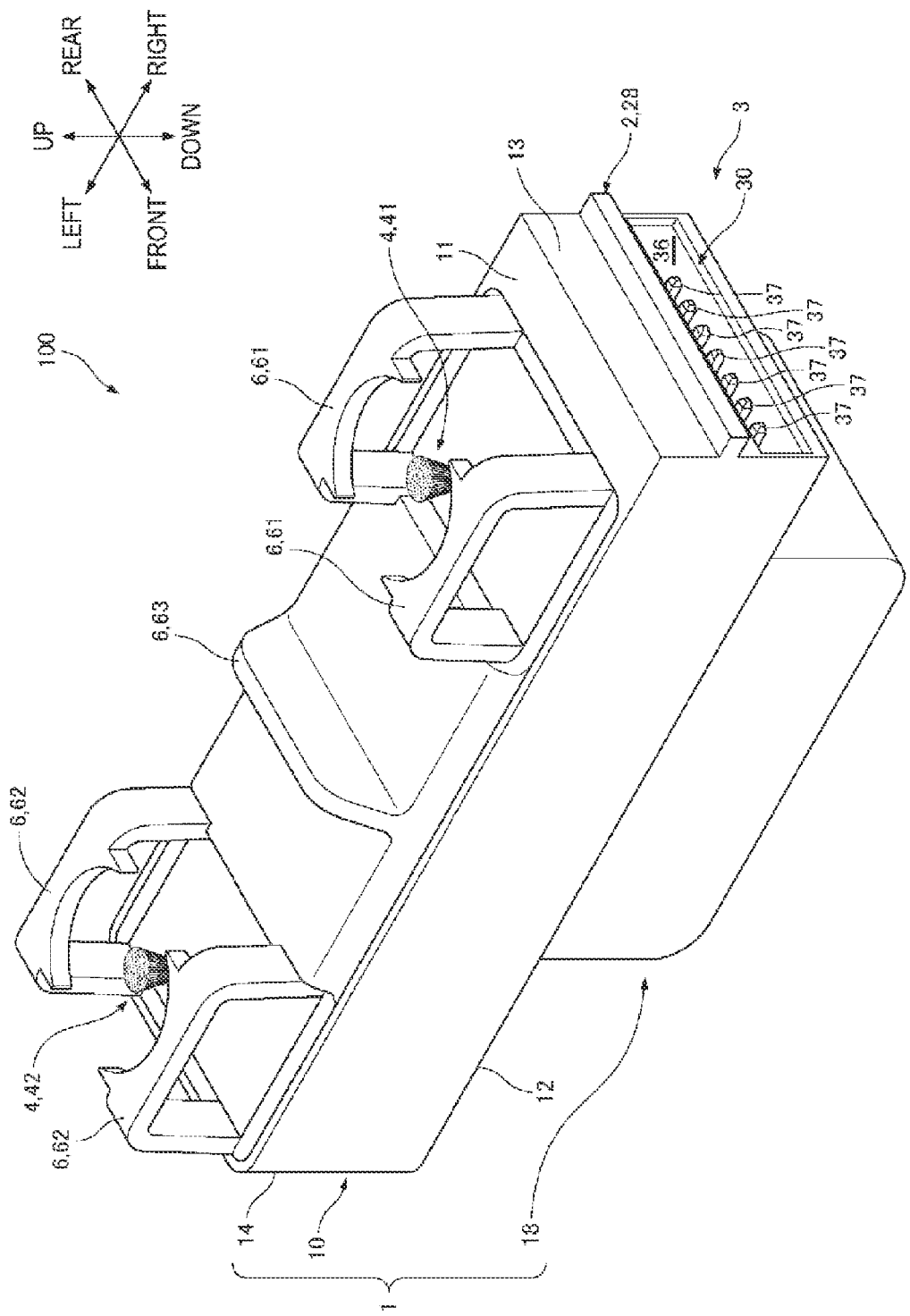
FIG. 5 is a perspective view illustrating a discharge device according to a third embodiment.

FIG. 5 is a perspective view illustrating the discharge device 100 of the third embodiment. As illustrated in FIG. 5, the step portion 2 is a projection 28 extending to the front end and the rear end of the main housing portion 10. With this configuration, the path of a high voltage that may propagate from the electrode portion 4 to the terminal portion 37 reliably passes through the projection 28. Therefore, it is possible to further prevent noise from being generated by the high voltage and adversely affecting peripheral components. In addition, since the step portion 2 is the projection 28, the strength of the housing portion 1 can be increased.

The step portion 2 included in the discharge device 100 of the third embodiment has been described as the projection 28 extending to the front end and the rear end of the main housing portion 10, but the step portion 2 may be a projection that does not reach the front end and the rear end of the main housing portion 10.

Fourth Embodiment

Next, a discharge device 100 according to a fourth embodiment of the disclosure will be described with reference to FIG. 6. In the fourth embodiment, the shape of the step portion 2 is different from that in the first to third embodiments. Differences between the fourth embodiment and the first to third embodiments will be described below.

Figure 6:
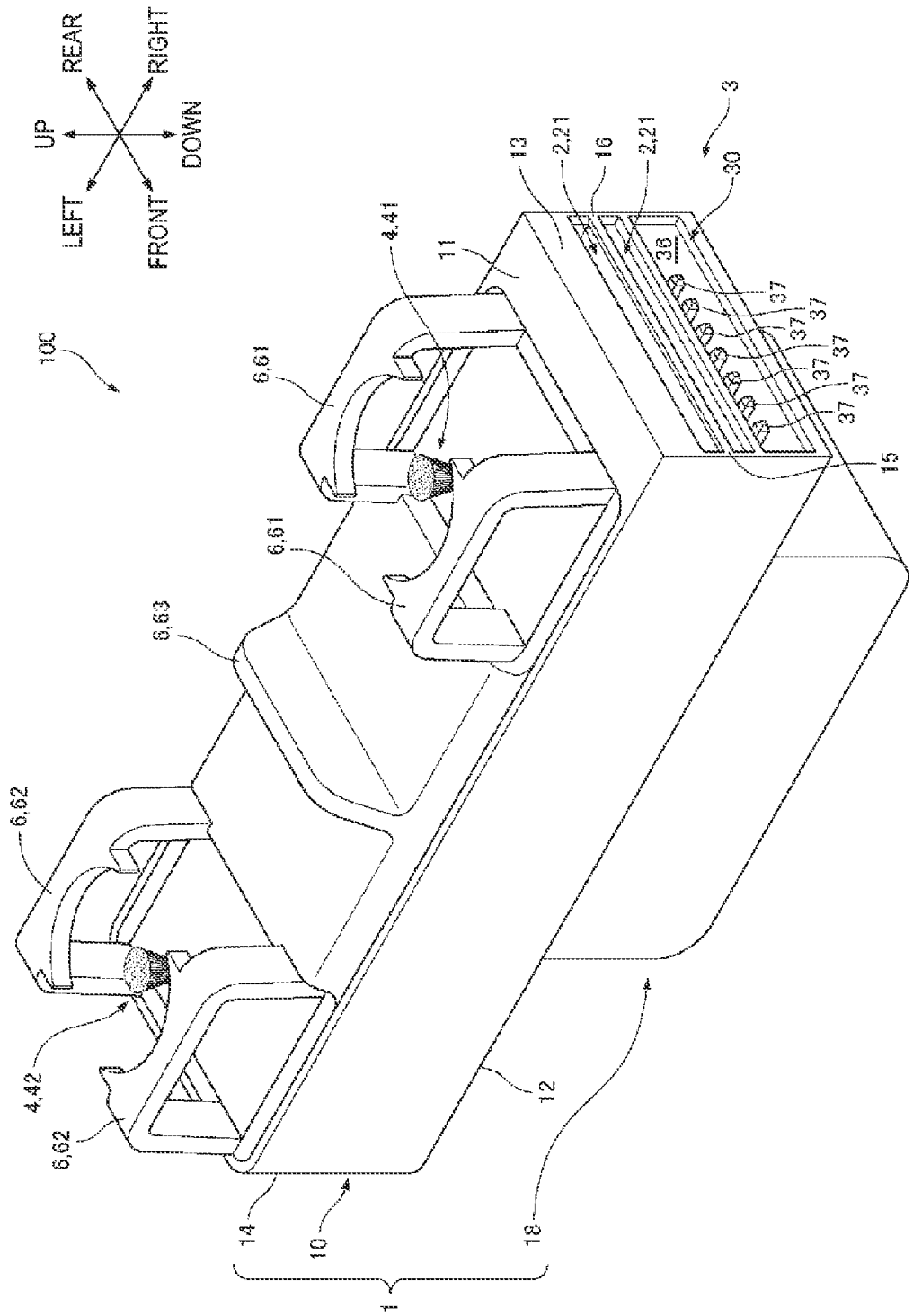
FIG. 6 is a perspective view illustrating a discharge device according to a fourth embodiment.

FIG. 6 is a perspective view illustrating the discharge device 100 of the fourth embodiment. As illustrated in FIG. 6, the step portion 2 is constituted of a plurality of recesses 21. Specifically, the step portion 2 is constituted of recesses 21 formed in two stages in the up-down direction. Neither of the recesses 21 in two stages reaches the front end or the rear end of the main housing portion 10. In other words, the recesses 21 in two stages are sandwiched in the front-rear direction between the front end piece 15 and the rear end piece 16 of the main housing portion 10.

Since the step portion 2 is constituted of the recesses 21 formed in two stages in the up-down direction, the creepage distance is further lengthened. Thus, a high voltage produced by discharge is less likely to propagate from the electrode portion 4 to the connector portion 3. As a result, it is possible to further prevent noise from being generated by the high voltage and adversely affecting the peripheral components.

The step portion 2 included in the discharge device 100 of the fourth embodiment has been described as the recesses 21 formed in two stages in the up-down direction, but the step portion 2 may be constituted of recesses 21 formed in three or more stages in the up-down direction. Each of the recesses 21 may be a recess 21 reaching the front end and rear end of the main housing portion 10. Furthermore, the step portion 2 may be constituted of projections 28 formed in two or more stages in the up-down direction.

Fifth Embodiment

Next, a discharge device 100 according to a fifth embodiment of the disclosure will be described with reference to FIG. 7. In the fifth embodiment, the shape of the step portion 2 is different from that in the first to fourth embodiments. Differences between the fifth embodiment and the first to fourth embodiments will be described below.

Figure 7:
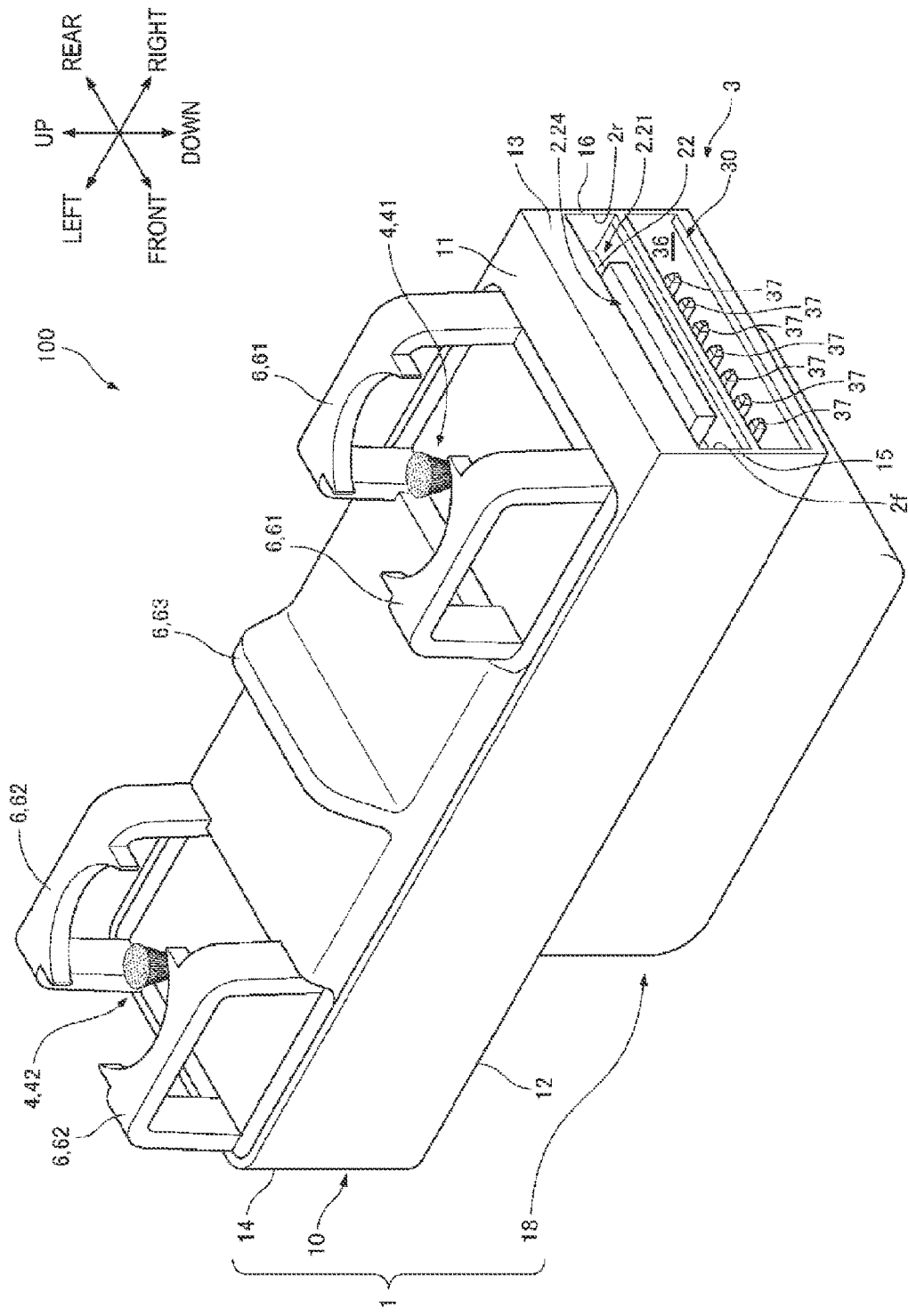
FIG. 7 is a perspective view illustrating a discharge device according to a fifth embodiment.

FIG. 7 is a perspective view illustrating the discharge device 100 of the fifth embodiment. As illustrated in FIG. 7, the step portion 2 is constituted of a recess 21 and a projection 24. The projection 24 is disposed in the recess 21. That is, the projection 24 projects rightward from a bottom 22 of the recess 21. The front end of the projection 24 does not reach a front end 2f of the recess 21, and the rear end of the projection 24 does not reach a rear end 2r of the recess 21. In other words, the front end and rear end of the projection 24 are in contact with none of the front end piece 15 and the rear end piece 16 of the main housing portion 10. The right end surface of the projection 24 is, for example, flush with the first side surface 13.

With this configuration, the step portion 2 not only further lengthens the creepage distance but also has a shape that can be easily held by an external holder (not illustrated). Thus, it is possible to further prevent noise from being generated by the high voltage and adversely affecting peripheral components, and the step portion 2 can be easily held by an external holder.

A portion (holding portion) by which the external holder holds the step portion 2 has a shape corresponding to the recess 21 of the step portion 2 and the projection 24 disposed in the recess 21 of the step portion 2. For example, the holding portion of the external holder has a shape that can be fitted into the recess 21 around the projection 24.

Note that the right end surface of the projection 24 of the step portion 2 included in the discharge device 100 of the fifth embodiment is not limited to being flush with the first side surface 13. For example, the right end surface of the projection 24 may be located further inward (further to the left) than the first side surface 13, or may be located further outward (further to the right) than the first side surface 13.

Sixth Embodiment

Next, a discharge device 100 according to a sixth embodiment of the disclosure will be described with reference to FIGS. 8 and 9. In the sixth embodiment, the shape of the step portion 2 is different from that in the first to fifth embodiments. Differences between the sixth embodiment and the first to fifth embodiments will be described below.

Figure 8:
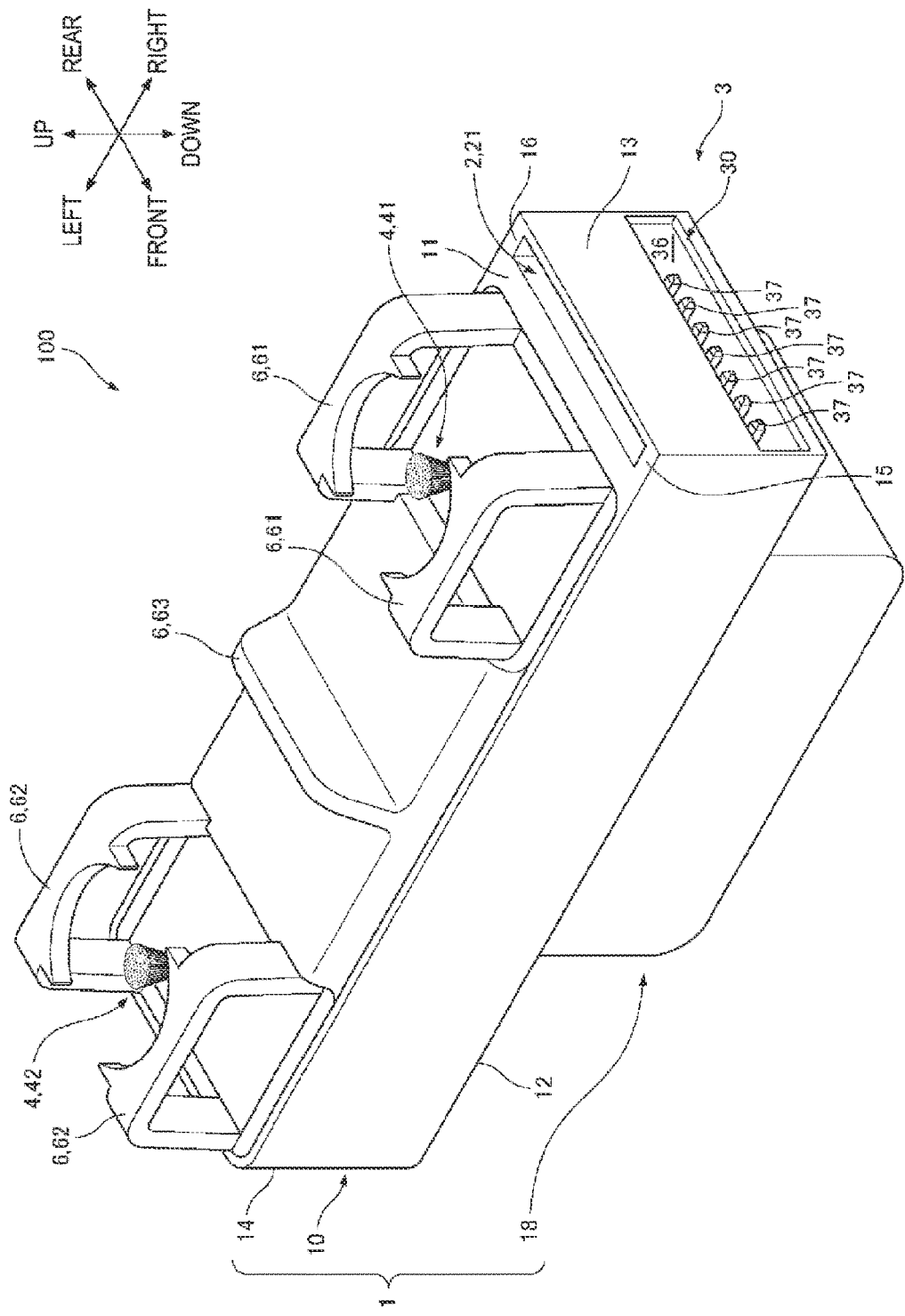
FIG. 8 is a perspective view illustrating a discharge device according to a sixth embodiment.
Figure 9:
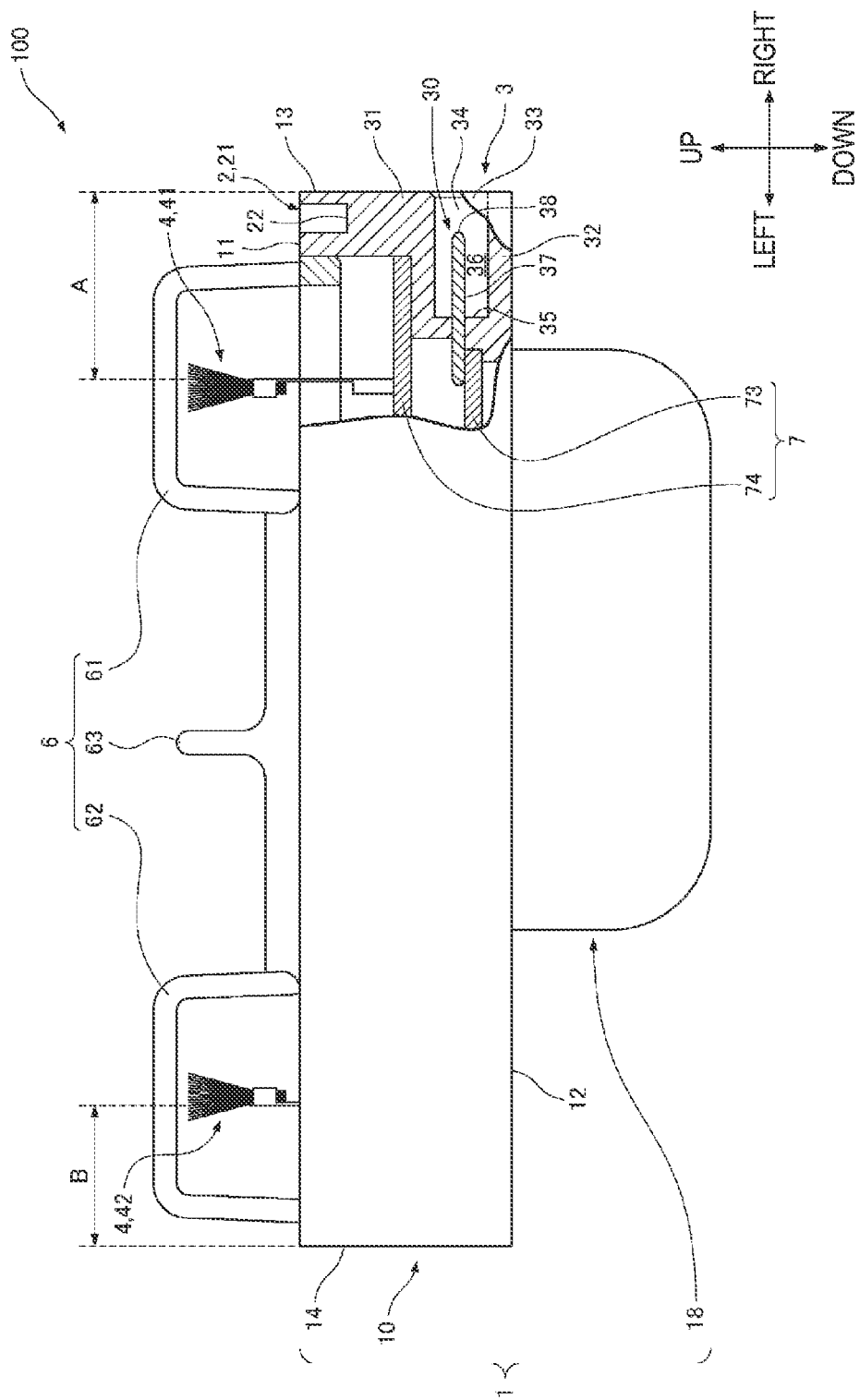
FIG. 9 is a partially cut-out front view illustrating the discharge device according to the sixth embodiment.

FIG. 8 is a perspective view illustrating the discharge device 100 of the sixth embodiment. FIG. 9 is a partially cut-out front view illustrating the discharge device 100 of the sixth embodiment. As illustrated in FIGS. 8 and 9, the step portion 2 is a recess 21 formed in the upper surface 11 of the housing portion 1. The recess 21 is disposed rightward relative to the right end of the electrode protecting section 6. The recess 21 does not reach the front end and rear end of the main housing portion 10. In other words, the recess 21 is sandwiched in the front-rear direction between the front end piece 15 and the rear end piece 16 of the main housing portion 10.

Since the recess 21, which is the step portion 2, is formed in the upper surface 11 of the main housing portion 10, the space in the main housing portion 10 is effectively utilized. Therefore, it is possible to further prevent noise from being generated by the high voltage and adversely affecting peripheral components, and the housing portion 1 may have a reasonable shape.

The step portion 2 included in the discharge device 100 of the sixth embodiment has been described as the recess 21 reaching neither the front end nor the rear end of the main housing portion 10, but the step portion 2 may be a recess 23 extending to the front end and the rear end of the main housing portion 10. The number of recesses 21 formed on the upper surface 11 of the main housing portion 10 is not limited to one, and may be two or more. Further, the step portion 2 disposed on the upper surface 11 of the main housing portion 10 may be constituted of one or more projections 28.

Seventh Embodiment

Next, a discharge device 100 according to a seventh embodiment of the disclosure will be described with reference to FIG. 10. In the seventh embodiment, the shape of a step portion 2 is different from those in the first to sixth embodiments. The point that differentiates the seventh embodiment from the first to sixth embodiments will be described below.

Figure 10:
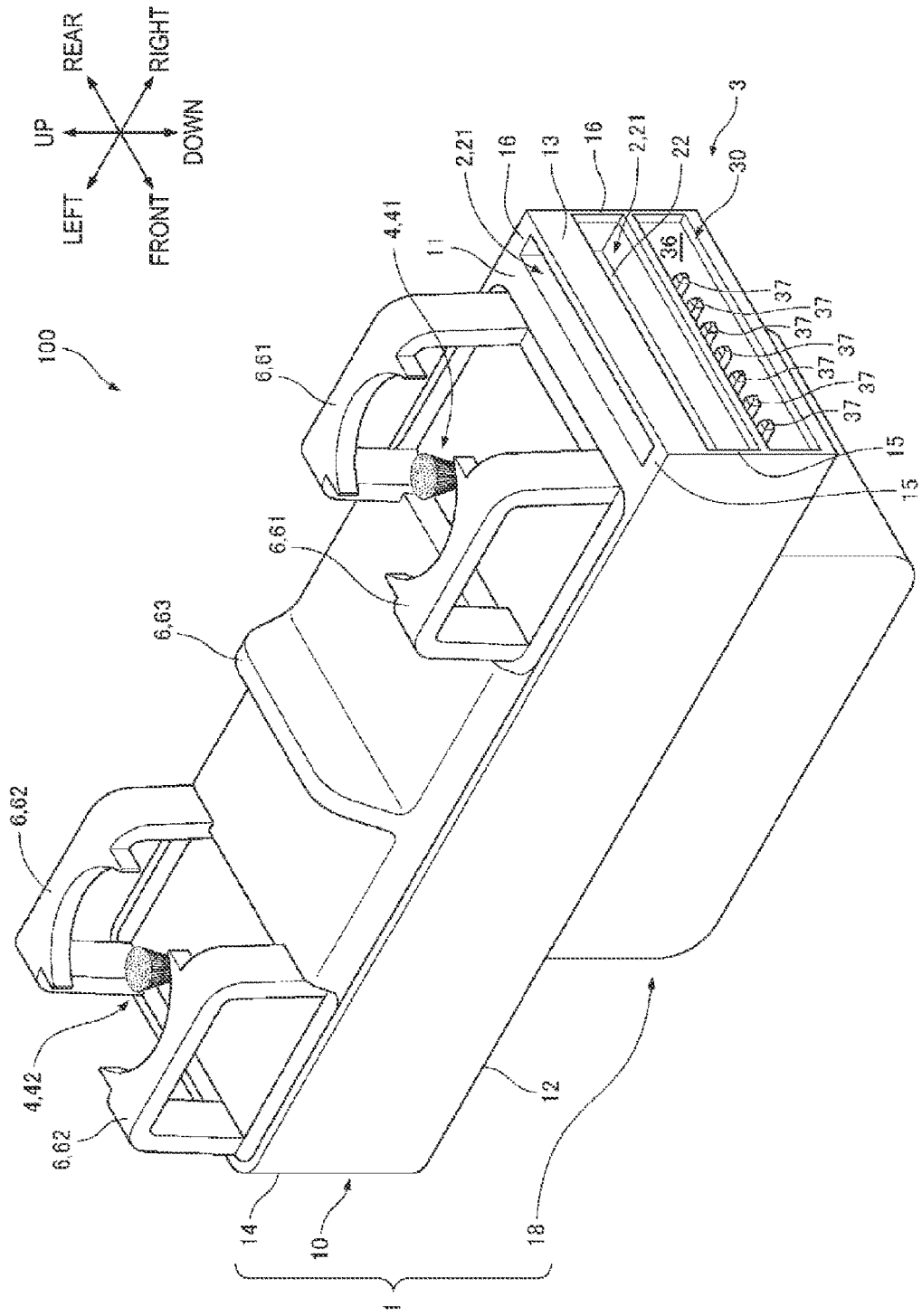
FIG. 10 is a perspective view illustrating a discharge device according to a seventh embodiment.

FIG. 10 is a perspective view illustrating the discharge device 100 of the seventh embodiment. As illustrated in FIG. 10, the step portion 2 is constituted of recesses 21 formed on an upper surface 11 and a first side surface 13 of a main housing portion 10, respectively. The recess 21 formed on the upper surface 11 is the same as the recess 21 described in the sixth embodiment. The recess 21 formed on the first side surface 13 is the same as the recess 21 described in the first embodiment. Therefore, it is possible to further prevented noise from being generated by the high voltage and adversely affecting peripheral components, and the housing portion 1 may have a reasonable shape.

Eighth Embodiment

Next, a discharge device 100 according to an eighth embodiment of the disclosure will be described with reference to FIG. 11. In the eighth embodiment, the shape of a step portion 2 is different from those in the first to seventh embodiments. The point that differentiates the eighth embodiment from the first to seventh embodiments will be described below.

Figure 11:
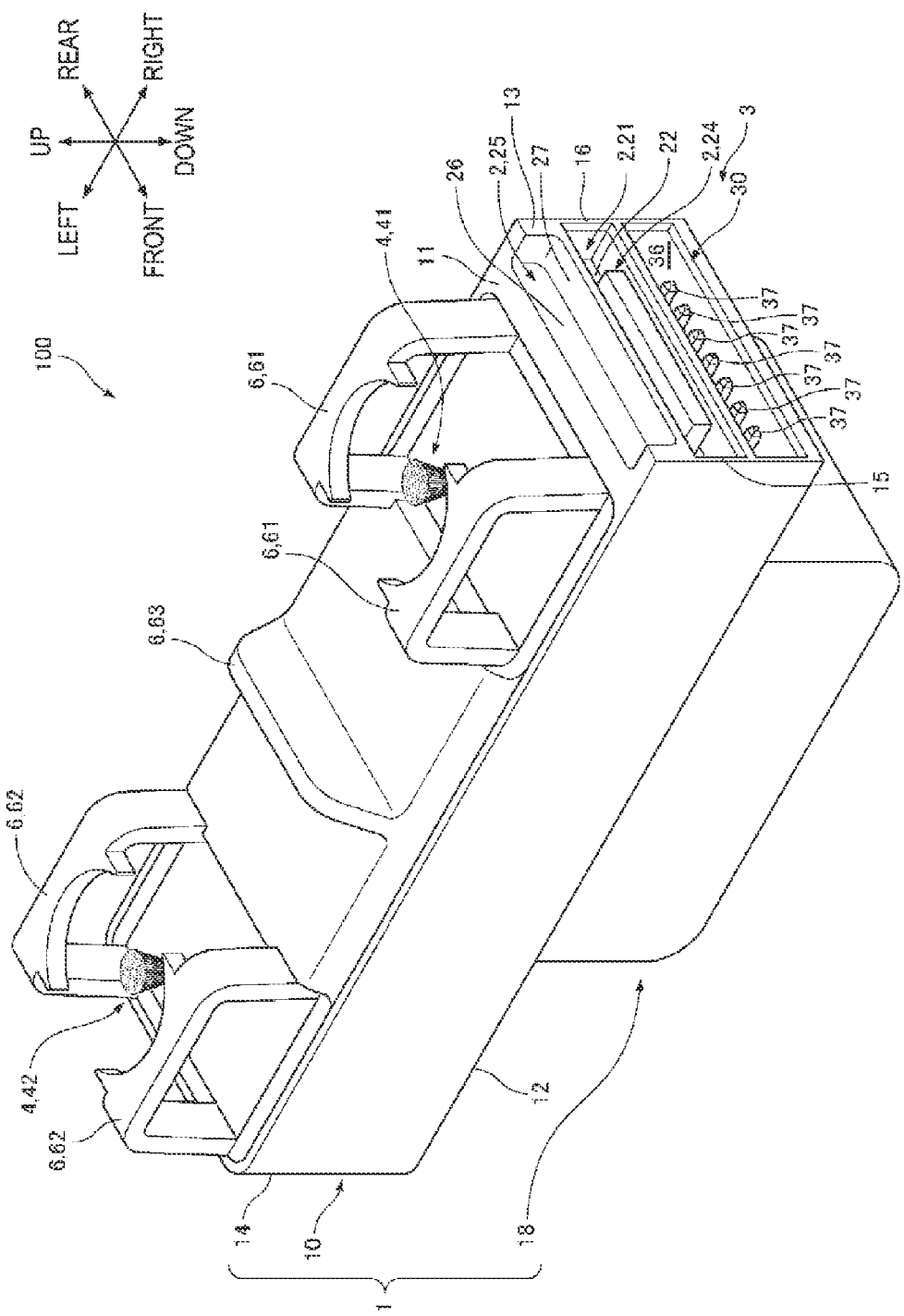
FIG. 11 is a perspective view illustrating a discharge device according to an eighth embodiment.

FIG. 11 is a perspective view illustrating the discharge device 100 of the eighth embodiment. As illustrated in FIG. 11, the step portion 2 is constituted of a corner recess 25, and the recess 21 and projection 24 described in the fifth embodiment. The corner recess 25 has such a shape that a corner formed by an upper surface 11 and a first side surface 13 in the main housing portion 10 is cut and removed. That is, the corner recess 25 is formed on the upper surface 11 and the first side surface 13 of the main housing portion 10. The corner recess 25 includes a longitudinal bottom 26 and a lateral bottom 27. The longitudinal bottom 26 is orthogonal to the upper surface 11 of the main housing portion 10. The lateral bottom 27 is orthogonal to the first side surface 13 of the main housing portion 10. The longitudinal bottom 26 and the lateral bottom 27 are continuously formed.

The corner recess 25, which constitutes the step portion 2, is disposed on the upper surface 11 and the first side surface 13 of the main housing portion 10, and thus the space of the main housing portion 10 is effectively utilized. Thus, the housing portion 1 may have a reasonable shape.

Thus, since the step portion 2 also includes the recess 21 and projection 24 described in the fifth embodiment, it is possible to further prevent noise from being generated by the high voltage and adversely affecting peripheral components, and the step portion 2 can be easily held by an external holder.

Embodiments of the disclosure have been described above with reference to the accompanying drawings. However, the disclosure is not limited to the embodiments described above, and the disclosure can be implemented in various modes without departing from the gist thereof. Further, various disclosures can be formed by appropriately combining a plurality of components disclosed in the embodiments described above. For example, several components may be deleted from all of the components described in the embodiments. Further, the components used from the first to eighth embodiments may be appropriately combined. Furthermore, the components across different embodiments may be appropriately combined. For ease of understanding, the drawings schematically illustrate each component as a main constituent, and the thickness, length, number, spacing, and the like of each component illustrated are different from the actual thickness, length, number, spacing for convenience of drawing preparation. Further, the speed, material, shape, dimensions, and the like of each component illustrated in the embodiments described above are one example and are not particularly limited, and various modifications can be made within a range that does not substantially deviate from the configuration of the disclosure.

(1) In the discharge device 100 of the first to eighth embodiments, the polarities of the first electrode 41 and the second electrode 42 are not described, and are not particularly limited. For example, the polarities of the first electrode 41 and the second electrode 42 may be different from each other, or may be the same.

(2) In the discharge device 100 of the first to eighth embodiments, the electrode portion 4 includes the first electrode 41 and the second electrode 42, but the electrode portion 4 is not limited thereto. For example, the electrode portion 4 may include only the first electrode 41 or the second electrode 42, or may include three or more electrodes.

(3) In the discharge device 100 of the first embodiment, the recess 21 is wider than the terminal portion 37 in the front-rear direction (2W>3W). However, being wider than the terminal portion 37 in the front-rear direction is not limited to the recess 21, and the same may also apply to portions of the step portion 2 other than the recess 21.

INDUSTRIAL APPLICABILITY

The disclosure provides a discharge device, and the provided discharge device has industrial applicability.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A discharge device, comprising:
a connector portion to which a voltage is applied externally;
an electrode portion configured to discharge by boosting and supplying the voltage from the connector portion; and
a housing portion housing the connector portion and the electrode portion,
wherein the housing portion includes a step portion between the connector portion and the electrode portion.

2. The discharge device according to claim 1, wherein the step portion includes a recess or a projection.

3. The discharge device according to claim 1, wherein the step portion includes a recess and a projection, and
the projection is disposed in the recess.

4. The discharge device according to claim 1, wherein the connector portion includes a terminal portion electrically connected to the electrode portion, and
the step portion is wider than the terminal portion in a direction intersecting a direction along a creepage distance between the electrode portion and the terminal portion.

5. The discharge device according to claim 1, wherein the housing portion further includes an upper surface on which the electrode portion is disposed, and a first side surface on which the connector portion is disposed, and
the step portion is disposed on the first side surface, or on the upper surface and the first side surface.

6. The discharge device according to claim 5, wherein the housing portion further includes a second side surface on a side opposite to the first side surface,
the electrode portion includes a first electrode closer to the first side surface than to the second side surface, and a second electrode closer to the second side surface than to the first side surface, and
a distance between the first electrode and the first side surface is longer than a distance between the second electrode and the second side surface.

* * * * *